US006175761B1

(12) United States Patent
Frandsen et al.

(10) Patent No.: US 6,175,761 B1
(45) Date of Patent: Jan. 16, 2001

(54) METHODS AND COMPUTER EXECUTABLE INSTRUCTIONS FOR RAPIDLY CALCULATING SIMULATED PARTICLE TRANSPORT THROUGH GEOMETRICALLY MODELED TREATMENT VOLUMES HAVING UNIFORM VOLUME ELEMENTS FOR USE IN RADIOTHERAPY

(75) Inventors: Michael W. Frandsen, Helena; Daniel E. Wessol, Bozeman, both of MT (US); Floyd J. Wheeler, Idaho Falls, ID (US)

(73) Assignee: Bechtel BWXT Idaho, LLC, Idaho Falls, ID (US)

( * ) Notice: Under 35 U.S.C. 154(b), the term of this patent shall be extended for 0 days.

(21) Appl. No.: 09/063,736

(22) Filed: Apr. 21, 1998

(51) Int. Cl.[7] ............................................. A61B 6/00
(52) U.S. Cl. ............................ 600/436; 128/920; 378/65
(58) Field of Search .................................. 600/407, 436; 128/920, 922; 250/363.03, 370.07; 378/64, 65; 382/128

(56) References Cited

U.S. PATENT DOCUMENTS

| | | | |
|---|---|---|---|
| 3,987,281 | 10/1976 | Hodes | 235/151.3 |
| 4,398,251 | * 8/1983 | LeMay | 364/414 |
| 4,675,150 | 6/1987 | Russell, Jr. et al. | 376/340 |
| 5,341,292 | 8/1994 | Zamenhof | 364/413.13 |
| 5,392,319 | 2/1995 | Eggers | 376/194 |
| 5,458,125 | 10/1995 | Schweikard | 128/653.1 |
| 5,548,694 | 8/1996 | Gibson | 395/124 |
| 5,630,786 | 5/1997 | Griffin et al. | 600/3 |

(List continued on next page.)

OTHER PUBLICATIONS

Nigg, David W., "Methods for Radiation Dose Distribution Analysis and Treatment Planning in Boron Neutron Capture Therapy," *Int. J. Radiation Oncology Biol. Phys.* vol. 28., No. 5, pp. 1121–1134, 1994.

*Primary Examiner*—Marvin M. Lateef
*Assistant Examiner*—Shawna J Shaw
(74) *Attorney, Agent, or Firm*—Workman Nydegger & Seeley

(57) ABSTRACT

Methods and computer executable instructions are disclosed for ultimately developing a dosimetry plan for a treatment volume targeted for irradiation during cancer therapy. The dosimetry plan is available in "real-time" which especially enhances clinical use for in vivo applications. The real-time is achieved because of the novel geometric model constructed for the planned treatment volume which, in turn, allows for rapid calculations to be performed for simulated movements of particles along particle tracks there through. The particles are exemplary representations of neutrons emanating from a neutron source during BNCT. In a preferred embodiment, a medical image having a plurality of pixels of information representative of a treatment volume is obtained. The pixels are: (i) converted into a plurality of substantially uniform volume elements having substantially the same shape and volume of the pixels; and (ii) arranged into a geometric model of the treatment volume. An anatomical material associated with each uniform volume element is defined and stored. Thereafter, a movement of a particle along a particle track is defined through the geometric model along a primary direction of movement that begins in a starting element of the uniform volume elements and traverses to a next element of the uniform volume elements. The particle movement along the particle track is effectuated in integer based increments along the primary direction of movement until a position of intersection occurs that represents a condition where the anatomical material of the next element is substantially different from the anatomical material of the starting element. This position of intersection is then useful for indicating whether a neutron has been captured, scattered or exited from the geometric model. From this intersection, a distribution of radiation doses can be computed for use in the cancer therapy. The foregoing represents an advance in computational times by multiple factors of time magnitudes.

35 Claims, 9 Drawing Sheets

U.S. PATENT DOCUMENTS

| | | | |
|---|---|---|---|
| 5,647,663 | 7/1997 | Holmes | 128/653.1 |
| 5,703,918 | 12/1997 | Hiismaki et al. | 376/458 |
| 5,870,697 * | 2/1999 | Chandler et al. | 702/179 |
| 5,976,066 * | 11/1999 | Yanch et al. | 600/1 |

* cited by examiner

METHODS AND COMPUTER EXECUTABLE INSTRUCTIONS FOR RAPIDLY CALCULATING SIMULATED PARTICLE TRANSPORT THROUGH GEOMETRICALLY MODELED TREATMENT VOLUMES HAVING UNIFORM VOLUME ELEMENTS FOR USE IN RADIOTHERAPY

CONTRACTUAL ORIGIN OF THE INVENTION

This invention was made with United States Government support under Contract No. DE-AC07-94ID13223, now Contract No. DE-AC07-99ID13727 awarded by the United States Department of Energy. The United States Government has certain rights in the invention.

BACKGROUND OF THE INVENTION

1. The Field of the Invention

The present invention relates generally to radiation therapy and specifically to the analytical computations for the dosimetric planning thereof. More specifically, the present invention relates to the macrodosimetry planning for specific radiotherapies such as neutron capture therapy, especially boron neutron capture therapy (BNCT), and fast neutron therapy having a BNCT component. Even more specifically, the present invention relates to methods and computer executable instructions for geometrically modeling a treatment volume planned for irradiation during various therapies and to calculating simulated particle transports through the model with simulation methods such as the Monte Carlo stochastic simulation method.

2. Copyrighted Materials

A portion of the disclosure of this patent document contains materials to which a claim of copyright protection is made. The copyright owner has no objection to the reproduction by anyone of the patent document or the patent disclosure as it appears in the Patent and Trademark Office patent file or records, but reserves all other rights with respect to the copyrighted work.

3. The Relevant Technology

Because significant improvements in radiobiological knowledge and encouraging human clinical results have recently been reported neutron radiotherapy modalities in the treatment of certain presently intractable malignancies are gradually becoming accepted practice.

Although application of neutrons for radiotherapy of cancer has been a subject of considerable clinical and research interest since the discovery of the neutron by Chadwick 1932, the earliest of clinical trials produced conspicuous failures. Since then, however, neutron radiotherapy has successfully evolved into a viable modality for treating inoperable salivary gland tumors and has emerged as a promising alternative for treating advanced prostate cancer, various lung tumors and certain other malignancies. Neutron capture therapy (NCT), a somewhat modified form of neutron radiotherapy, has entered clinical trials as a modality in treating glioblastoma multiforme and metastic malignant melanoma.

The basic physical process involved in past neutron therapy and neutron capture therapy differs in several respects. In fast neutron therapy, neutrons having relatively high energy (approximately 30 to 50 MeV) are generated by a suitable neutron source and used directly for irradiation of the treatment volume, as is done with standard photon (X-ray) therapy. In NCT, a neutron capture agent is introduced into a patient and is selectively taken into the malignant tissue. The administration of a pharmaceutical containing the neutron capture agent is preferably accomplished by a directed administration into the blood stream of the patient. At an appropriate time after administration of the neutron capture agent, the treatment volume (i. e., the anatomical structure to be treated) is exposed to a field of thermal neutrons produced by application of an external neutron beam. Because boron-10 has a large cross sectional area particularly suited for the capture of thermal neutrons (neutrons having energy less than 0.5 eV), boron-10 has preferentially become the capture agent of choice. Thus, the technology is commonly referred to as boron neutron capture therapy or BNCT.

BNCT is based on the nuclear reaction that occurs when boron 10, a non-radioactive isotope that accounts for approximately one-fifth of natural occurring boron, is irradiated with and absorbs or "captures" neutrons. Because the thermal neutrons that it captures are of such low energy they cause little tissue damage as compared with other forms of radiation such as protons, gamma rays, and fast neutrons. When an atom of boron 10 captures a neutron, an unstable isotope, boron 11, forms. The boron 11 instantly fissions yielding lithium-7 nuclei and energetic alpha particles (helium-4). The average total energy of this charged particle pair is about 2.35 MeV which is a highly lethal form of radiation. Yet, since these alpha particles have a path length of about ten microns (about 1 cell diameter), BNCT offers the advantage of cancer cell neutralization with only limited damage to nearby tissues. Moreover, BNCT does not rely on the capture of numerous neutrons because it only takes a few particles releasing their energy within a cancer cell to destroy it.

Another form of neutron radiotherapy is also the subject of current research interest. This other form is essentially a hybrid that combines the features of fast neutron therapy and NCT. In this type of therapy, a neutron capture agent is introduced into a patient, preferably into the malignant tissue only. This treatment is prior to the administration of standard fast neutron therapy. Because a small fraction of the neutrons in fast neutron therapy will be thermalized in the irradiation volume, it is possible to obtain a small incremental absorbed dose from the neutron capture interactions that result. Thus, based on current radiobiological research, improved tumor control appears to be likely when using this augmentation concept.

No matter which radiotherapy modality is used, some basic elements exist in the analytical computation of the macroscopic dosimetry, or macrodosimetry, thereof. With respect to BNCT therapy, for example, the essence of all analytical macrodosimetry is found by solving the three dimensional Boltzmann transport equation for neutral particles given certain descriptive information as input. This descriptive information consists generally of: (i) a geometric model of the irradiation volume; (ii) a mathematical description of the treatment neutron beam; and (iii) and a complete set of coupled neutron and photon interaction cross section data for all significant elements within the irradiation volume.

The geometric model of the patient and simulation of the irradiation will be discussed subsequently. As for the neutron beam, the description consists primarily of the neutron and photon spectra, angular distributions, and spatial intensity distributions in a defined plane of incidence (usually the exit port of the treatment beam collimator). This description is ordinarily constructed from a combination of calculational and experimental data pertinent to the beam of interest. Neutron and photon cross sections are typically taken from standard data collections such as the Evaluated Nuclear Data File (ENDF) and pre-processed into an appropriate multi-group or continuous-energy format.

Given the neutron and photon fluxes throughout the treatment volume (i.e., the complete space and energy-dependent solution of the Boltzmann equation for the situation of interest), the corresponding macroscopic absorbed dose distribution is ordinarily constructed by: (i) multiplying the calculated energy-dependent flux data by appropriate energy-dependent flux-to-dose conversion factors for each radiation dose component; (ii) integrating over the neutron or photon energy range as appropriate; and (iii) summing all components.

Two fundamentally different methods are available for computing the neutron and photon fluxes throughout the treatment volume. The first method is the Monte Carlo Stochastic Simulation Method which is presently preferred since the complex geometries that are characteristic of biological systems can be very accurately represented. The second method is a deterministic method based on direct numerical solution of the transport equation. Although the methods can be complimentary in terms of detailed spatial dose-distributions and dose-volume histogram information, both methods have their own appropriate uses, to which, only the stochastic methods will be used to describe the problem herein.

The stochastic methods for determining neutron and photon fluxes throughout the treatment volume are conceptually very simple, but the actual mathematical implementations for each particular method have attained high degrees of theoretical sophistication.

For BNCT purposes, the basic idea is to solve the fixed-source form of the transport equation by randomly selecting neutrons and photons from a specified boundary source (i.e., the incident neutron beam) and following each selected particle through the calculational geometry until it is either captured or is exited from the irradiation volume of interest. With reference to FIG. 1, this is depicted generally as method 100.

Typically, this method is performed by obtaining pertinent medical imagery of the treatment area of interest (step 102) generated by well known means such as by Computed Tomography (CT), Magnetic Resonance (MR) imaging, gamma cameras or positron emission tomography (PET). Then, at step 104, modeling the imagery by one of the methods subsequently described. At step 106, calculating the fluxes from simulations of individual particles (i.e., generated by the neutron source or beam) being transported through the model.

With reference to FIG. 2, once modeled, the step 106 of calculating simulated particles transported through the model begins with determining an initial position and velocity vector for each particle, step 108. The uniquely corresponding path of movement for a particle throughout the model, as dictated by its velocity vector, will be described herein as a particle track. The particular particle track is selected as a multi-dimensional probability distribution function based on a series of machine-generated pseudo numbers generated in a well known manner by Monte Carlo simulation.

At step 110, the distance that each particle must traverse to reach the nearest boundary region is then determined. At step 112, another pseudo random number is used to determine whether the particle indeed reaches the next boundary condition or interacts with the medium of the boundary condition first. The probability of interaction is established by the local neutron or photon cross section of the medium as appropriate. If, at step 112, the particle reaches the next boundary condition, the process continues into the next region and the step 110 is reiterated. If, on the other hand, at step 112, an interaction occurs and the particle on its particle track does not reach the next boundary condition, at step 114 another pseudo random number is used to determine the particle status or type of interaction, i.e., particle capture, exit or scatter.

If particle capture occurs, the particle track is terminated and simulated particle transports are typically calculated for the secondary gammas that are emitted during the neutron capture interaction, step 116. If the particle is scattered, a new or updated velocity vector is determined for the particle and the particle track continues from the position where the scatter occurred (step 118). If the particle is exited from the model, the particle track/transport simulation is terminated at step 120. Eventually all particles are either captured or exited from the model. For each particle track, a scalar flux (track length per unit volume) generated by the particle is tallied as it traverses the geometry. If enough particles are followed, statistically converged estimates of the particle flux in each region of interest can be obtained.

A first method for generating a geometric model from medical imagery is based on "voxel" reconstruction techniques and is exemplified in U.S. Pat. No. 5,341,292 issued to Zamenhoff in August of 1994, assigned to New England Medical Center. In general, each medical image slice, such as those generated by CT, is partitioned into "squares" approximately 1 cm on a side. Thereafter, each of the squares are mathematically stacked into a 3-D array of "voxels" (1 cm$^3$) that can be supplied to a general-purpose Monte Carlo code, such as Monte Carlo for neutron and photon transport (MCNP), for purposes of simulating particle transport there through.

One problem with this method is that the voxel is very large in comparison to each pixel of information in the medical image, e.g, each voxel may equal 500 pixels. Thus, the voxel model does not utilize all known information. Ultimately, this limits the dosimetry planning for actual patients.

Another problem is that each voxel can only represent limited variations in the anatomical materials of a patient in order to make the particle transport simulations time-manageable. In particular, each voxel represents only one of four materials, either bone, normal soft tissue, tumor soft tissue and air. Further, each of the four materials can only be represented in amounts of 0, 20, 40, 60, 80 and 100 percentages. Given this constraint, only 56 total possible material combinations can exist even though the actual anatomical material within the patient is more complex than this model would suggest. Thus, the model is not mapped as precise as possible to an actual patient. Again, the dosimetry planning is restricted by the inaccuracy of the model.

Even with the usage of limited material combinations and limited percentages thereof, the lauded computational CPU time for three separate "runs" of typically 500,000 starting particles/run, for one neutron beam, was 70 hours. Although it is presently reported that the computational times have decreased since the issue of the patent, the computational times are still typically numerous hours in length. Since time is critical in the dosimetry planning for in vivo applications during clinical use, these computational times are still unacceptably long. Moreover, this patent teaches that although reductions in the volume of the voxel will improve the fidelity of the model, reductions in volume will adversely create a "costly tradeoff in terms of computation time" and memory.

Still another problem stems from modeling complex curved surfaces that describe anatomical structures of interest by mere approximations of combinations of orthogonal voxel facets. Because of this feature, it is not possible to simultaneously preserve both the enclosed volume and the surface area of the structures being modeled.

A second method for generating a geometric model from medical imagery is based on the calculation of non-uniform rational B-spline fits to the various tissue compartment surfaces. This method is exemplified in the special purpose BNCT-edition Monte Carlo software system for medical dosimetry developed by the Idaho National Engineering Laboratory (INEL) with assistance from the computer science departments of the Universities of Utah and Montana State. With this method, regions of interest (skin, skull, brain, tumor, etc.) are outlined directly on the medical image with the assistance of computer-displayed medical images. Thereafter, the outlined regions are mathematically combined to produce detailed surface equations describing the 3-D surfaces that enclose the volume of interest. These surface equations are subsequently used with the Monte Carlo simulation methods.

Still another method for generating a geometric model of the irradiation volume uses combinations of small numbers of geometric primitives representable by simple surface equations. Such primitives include spheres, cubes, cylinders, ellipsoids, etc. This method, however, suffers shortcomings because the irradiation volume modeled is merely an approximation, not based on any medical imagery, and cannot accurately represent an optimized dosimetry plan for in vivo applications.

Accordingly, it is desirous to improve the computational methods used in macrodosimetry planning, especially by improving computational times, without sacrificing any of the presently known accuracies thereof.

OBJECTS AND SUMMARY OF THE INVENTION

It is, therefore, an object of the present invention to provide improved methods for analytically computing dosimetry plans for use in radiotherapy planning.

It is another object of the present invention to improve methods for geometrically modeling a planned irradiation volume and for calculating simulated particle transport through the model.

It is still another object of the present invention to improve methods for geometrically modeling a planned irradiation volume by using all available anatomical information for various structures in the volume.

It is yet another object of the present invention to decrease the computational times required for calculating simulated particle transport through a geometrically modeled irradiation volume, especially during clinical use for in vivo applications.

It is still yet another object of the present invention to provide improved methods for geometrically modeling a planned irradiation volume and for calculating simulated particle transport through the model without sacrificing any presently known accuracies thereof.

It is a further object of the present invention to provide improved geometric models for planned irradiation volumes that more closely approximate pertinent medical imagery.

It is an even further object of the present invention to provide improved methods of geometrically modeling planned irradiation volumes by using any available pertinent medical imagery.

It is still a further object of the present invention to provide improved methods for geometrically modeling a planned irradiation volume that does not substantially inhibit calculational times for simulated particle transport through the model as additional geometric elements used in the model are added in large quantities to the model.

It is still yet a further object of the present invention to provide computer executable instructions suitable for use in various computing system configurations that accomplish the foregoing objectives.

In accordance with the invention as embodied and broadly described herein, the foregoing and other objectives are achieved by providing methods and computer executable instructions for ultimately developing a dosimetry plan for a treatment volume targeted for irradiation during cancer therapy. The dosimetry plan is available in "real-time" which especially enhances clinical use for in vivo applications. The real-time is achieved because of the novel geometric model constructed for the planned treatment volume which, in turn, allows for rapid calculations to be performed for simulated movements of particles along particle tracks there through. The particles are exemplary representations of neutrons emanating from a neutron source during BNCT.

In a preferred embodiment, a medical image having a plurality of pixels of information representative of a treatment volume is obtained. The pixels are: (i) converted into a plurality of substantially uniform volume elements having substantially the same shape and volume of the extended pixels; and (ii) arranged into a geometric model of the treatment volume. An anatomical material associated with each uniform volume element is defined and stored. Thereafter, a movement of a particle along a particle track is defined through the geometric model along a primary direction of movement that begins in a starting element of the uniform volume elements and traverses to a next element of the uniform volume elements. The particle movement along the particle track is effectuated in integer based increments until a position of intersection occurs that represents a condition where the anatomical material of the next element is substantially different from the anatomical material of the starting element. This position of intersection is then useful for indicating whether a neutron has been captured, scattered or exited from the geometric model. From this intersection, a distribution of radiation doses can be computed for use in the cancer therapy. The foregoing represents an advance in computational times by multiple factors of time magnitudes.

These and other objects and features of the present invention will become more fully apparent from the following description and appended claims, or may be learned by the practice of the invention as set forth hereinafter.

BRIEF DESCRIPTION OF THE DRAWINGS

In order to more fully understand the manner in which the above-recited and other advantages and objects of the invention are obtained, a more particular description of the invention will be rendered by reference to specific embodiments thereof which are illustrated in the appended drawings. Understanding that these drawings depict only typical embodiments of the invention and are not therefore to be considered to be limiting of its scope, the invention in its presently understood best mode for making and using the same will be described and explained with additional specificity and detail through the use of the accompanying drawings in which.

DETAILED DESCRIPTION OF THE PREFERRED EMBODIMENTS

The present invention relates to methods and computer executable instructions for ultimately developing a dosimetry plan for a treatment volume targeted for irradiation during cancer therapy. It is a feature of the present invention that this dosimetry plan is available in "real-time" which especially enhances clinical use for in vivo applications. The real-time is achieved because of the novel geometric model constructed for the planned treatment volume which, in turn, allows for rapid calculations to be performed for simulated movements of particles along particle tracks there through. The particles are exemplary representations of neutrons emanating from a neutron source during BNCT, but should not be construed as limited thereto.

In accordance with the present invention, diagrams are used herein to illustrate either the structure or processing of embodiments used to implement the system and method of the present invention. Using the diagrams in this manner to present the invention, however, should not be construed as limiting of its scope but merely as representative.

Figure 3:
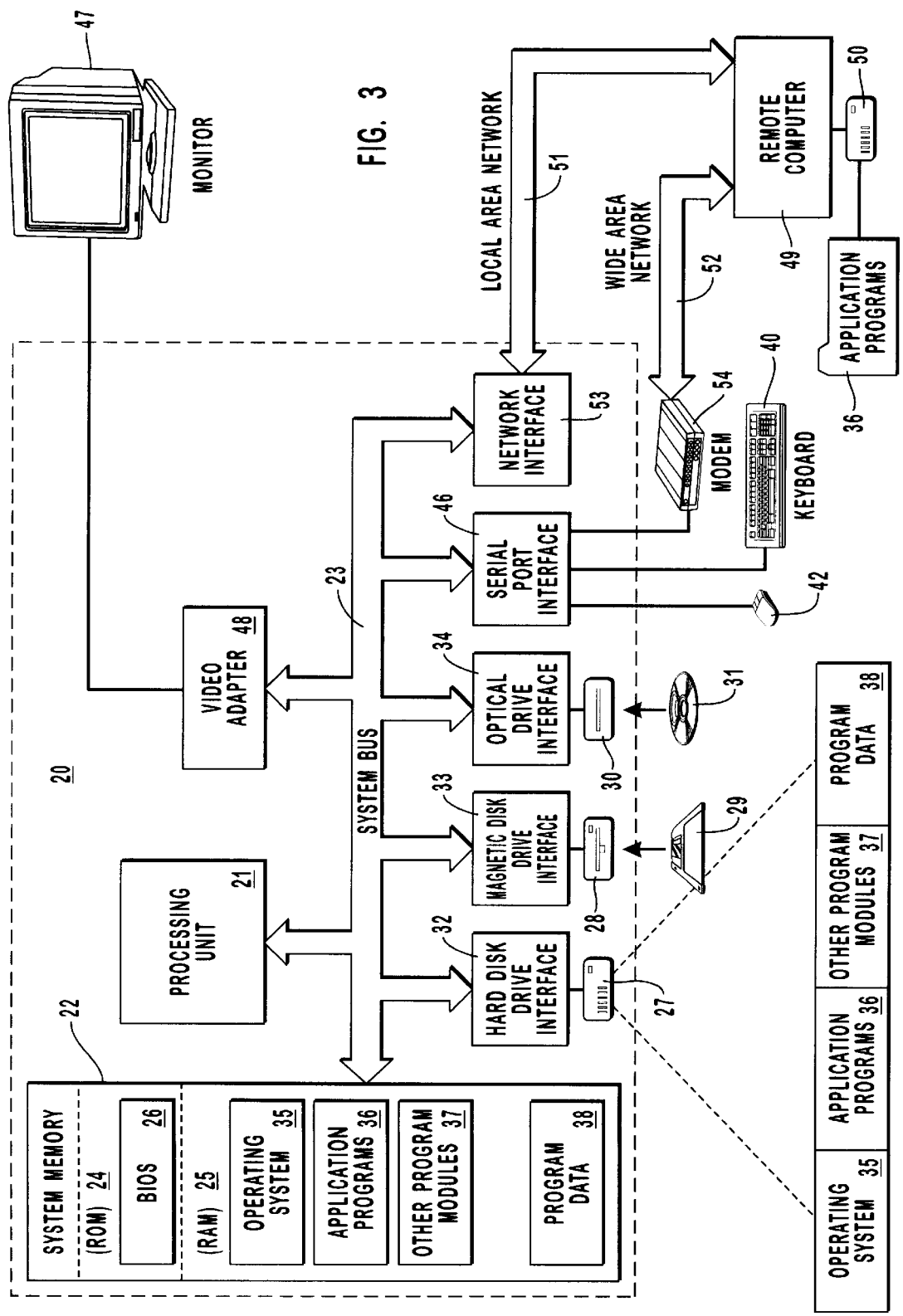
FIG. 3 is an exemplary system for providing a suitable operating environment for the present invention.

FIG. 3 and the following discussion are intended to provide a brief, general description of a suitable computing environment in which either the structure or processing of embodiments may be implemented. Since the following may be computer implemented, particular embodiments may range from computer executable instructions as part of computer readable media to hardware used in any or all of the following depicted structures. Implementation may additionally be combinations of hardware and computer executable instructions.

When described in the context of computer readable media having computer executable instructions stored thereon, it is denoted that the instructions include program modules, routines, programs, objects, components, data structures, etc. that perform particular tasks or implement particular abstract data types upon or within various structures of the computing environment. Executable instructions exemplarily comprise instructions and data which cause a general purpose computer, special purpose computer, or special purpose processing device to perform a certain function or group of functions.

The computer readable media can be any available media which can be accessed by a general purpose or special purpose computer. By way of example, and not limitation, such computer readable media can comprise RAM, ROM, EEPROM, CD-ROM or other optical disk storage, magnetic disk storage or other magnetic disk storage devices, or any other medium which can be used to store the desired executable instructions or data fields and which can be accessed by a general purpose or special purpose computer. Combinations of the above should also be included within the scope of computer readable media. For brevity, computer readable media having computer executable instructions may sometimes be referred to as "software" or "computer software."

With reference to FIG. 3, an exemplary system for implementing the invention includes a general purpose computing device in the form of a conventional computer 20. The computer 20 includes a processing unit 21, a system memory 22, and a system bus 23 that couples various system components including the system memory to the processing unit 21. The system bus 23 may be any of several types of bus structures including a memory bus or memory controller, a peripheral bus, and a local bus using any of a variety of bus architectures. The system memory includes read only memory (ROM) 24 and random access memory (RAM) 25. A basic input/output system (BIOS) 26, containing the basic routines that help to transfer information between elements within the computer 20, such as during start-up, may be stored in ROM 24. The computer 20 may also include a magnetic hard disk drive 27 for reading from and writing to a hard disk, not shown, a magnetic disk drive 28 for reading from or writing to a removable magnetic disk 29, and an optical disk drive 30 for reading from or writing to removable optical disk 31 such as a CD-ROM or other optical media. The hard disk drive 27, magnetic disk drive 28, and optical disk drive 30 are connected to the system bus 23 by a hard disk drive interface 32, a magnetic disk drive-interface 33, and an optical drive interface 34, respectively. The drives and their associated computer-readable media provide nonvolatile storage of computer readable instructions, data structures, program modules and other data for the computer 20.

Although the exemplary environment described herein employs a hard disk, a removable magnetic disk 29 and a removable optical disk 31, it should be appreciated by those skilled in the art that other types of computer readable media which can store data accessible by a computer include magnetic cassettes, flash memory cards, digital video disks, removable disks, Bernoulli cartridges, random access memories (RAMs), read only memories (ROM), and the like.

Other storage devices are also contemplated as available to the exemplary computing system. Such storage devices may comprise any number or type of storage media including, but not limited to, high-end, high-throughput magnetic disks, one or more normal disks, optical disks, jukeboxes of optical disks, tape silos, and/or collections of tapes or other storage devices that are stored off-line. In general, however, the various storage devices may be partitioned into two basic categories. The first category is local storage which contains information that is locally available to the computer system. The second category is remote storage which includes any type of storage device that contains information that is not locally available to a computer system. While the line between these two categories of devices may not be well defined, in general, local storage has a relatively quick access time and is used to store frequently accessed data, while remote storage has a much longer access time and is used to store data that is accessed less frequently. The capacity of remote storage is also typically an order of magnitude larger than the capacity of local storage.

A number of program modules may be stored on the hard disk, magnetic disk 29, optical disk 31, ROM 24 or RAM 25, including an operating system 35, one or more application programs 36, other program modules 37, and program data 38. Such application programs may include, but are not limited to, random generation modules, such as Monte Carlo simulators and graphic modules or modeling modules for generating graphics and models for user display. A user may enter commands and information into the computer 20 through input devices such as a keyboard 40 and pointing device 42. Other input devices (not shown) may include a microphone, joy stick, game pad, satellite dish, scanner, or the like. These and other input devices are often connected to the processing unit 21 through a serial port interface 46 that is coupled to system bus 23, but may be connected by other interfaces, such as a parallel port, game port or a universal serial bus (USB). A monitor 47 or other type of display device is also connected to system bus 23 via an interface, such as video adapter 48. In addition to the monitor, computers often include other peripheral output devices (not shown), such as speakers and printers. Scanner peripheral devices (not shown) for reading imagery into the computer are often also included.

The computer 20 may operate in a networked environment using logical connections to one or more other computing configurations, such as remote computer 49. Remote computer 49 may be a personal computer, a server, a router, a network PC, a peer device or other common network node, and typically includes many or all of the elements described above relative to the computer 20, although only a memory storage device 50 has been illustrated in FIG. 6. The logical connections depicted in FIG. 3 between the computer 20 and the remote computer 49 include a local area network (LAN) 51 and a wide area network (WAN) 52 that are presented here by way of example and not limitation. Such networking environments are commonplace in offices with enterprise-wide computer networks, intranets and the Internet.

When used in a LAN networking environment, the computer 20 is connected to the local network 51 through a network interface or adapter 53. When used in a WAN networking environment, the computer 20 typically includes a modem 54 or other means for establishing communications over the wide area network 52, such as the Internet. The modem 54, which may be internal or external, is connected to the system bus 23 via the serial port interface 46. In a networked environment, program modules depicted relative to the computer 20, or portions thereof, may be stored in the local or remote memory storage devices and may be linked to various processing devices for performing certain tasks. It will be appreciated that the network connections shown are exemplary and other means of establishing a communications link between the computers may be used.

Moreover, those skilled in the art will appreciate that the invention may be practiced with other computer system configurations, including hand-held devices, multi-processor systems, microprocessor-based or programmable consumer electronics, network PCs, minicomputers, computer clusters, mainframe computers, and the like.

Figure 4:
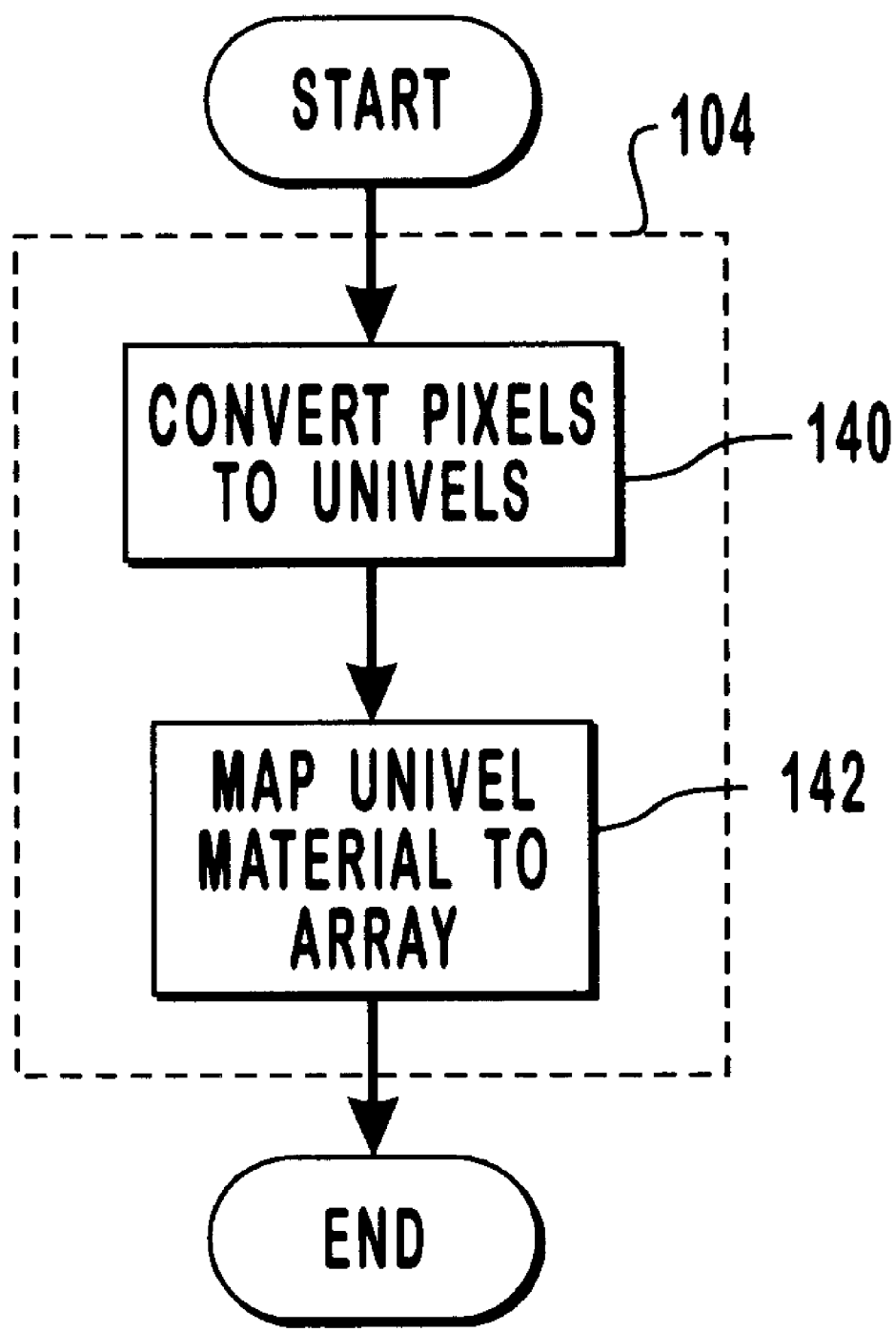
FIG. 4 is a flow diagram for geometrically modeling pertinent medical imagery in accordance with the present invention.

With reference to FIG. 4, a flow diagram for modeling imagery (step 104) in accordance with the present invention comprises the steps of: (i) converting pixels to "univels," step 140; and (ii) mapping univels to an array, step 142.

It should be appreciated that medical imagery is generated and obtained from numerous and diverse sources, such as CT, MRI and PET. In general, these sources generate an image of a structure by making a series of plane cross-sectional slices along a common axis. Some of these sources provide resolutions of 256×256 pixels of information by about 40 axial slices, such as with CT. Some have finer resolution like 512×512 pixels of information by about 512 axial slices.

Since these sources provide the medical imagery in the form of pixels of information, it is a feature of this invention to directly convert these pixels into "elements" from which a geometric model can be produced. Preferably, these elements are of the substantially same shape and volume as the pixel of information. In this manner, valuable time in configuring the geometric model is preserved and no loss of accuracy is introduced because of the direct one-to-one correspondence between a pixel of information and the modeling element. As used herein, these elements are referred to as uniform volume elements or "univels" and are proportional representations of the pixels they represent. Other attributes include a substantially uniform volume as between all elements.

Since typical medical imagery provides pixels in about 1 mm×1 mm×5 mm right parallelepipeds, the preferred univels have this same shape and volume. The conversion from pixels to univels can efficaciously be accomplished with a pixel paint program or a filling between non-uniform rational B-spline (NURBS) surfaces. Once converted, and given the foregoing dimensions of medical imagery, a computer would need only approximately 2.6 MB of storage space for a 256×256×40 medical image set and 134 MB of storage space for a 512×512×512 medical image set. Although 134 MB of storage space is relatively large, this is quite affordable given the configurations of computing systems presently used.

Inherent with a pixel of information in a medical image is an anatomical material, such as bone, soft tissue, blood, etc. Such materials are broad ranging and are often identified with bytes of information. Whatever the anatomical material, each univel is associated with a material and is mapped to an array or simply stored at step 142.

Figure 5:
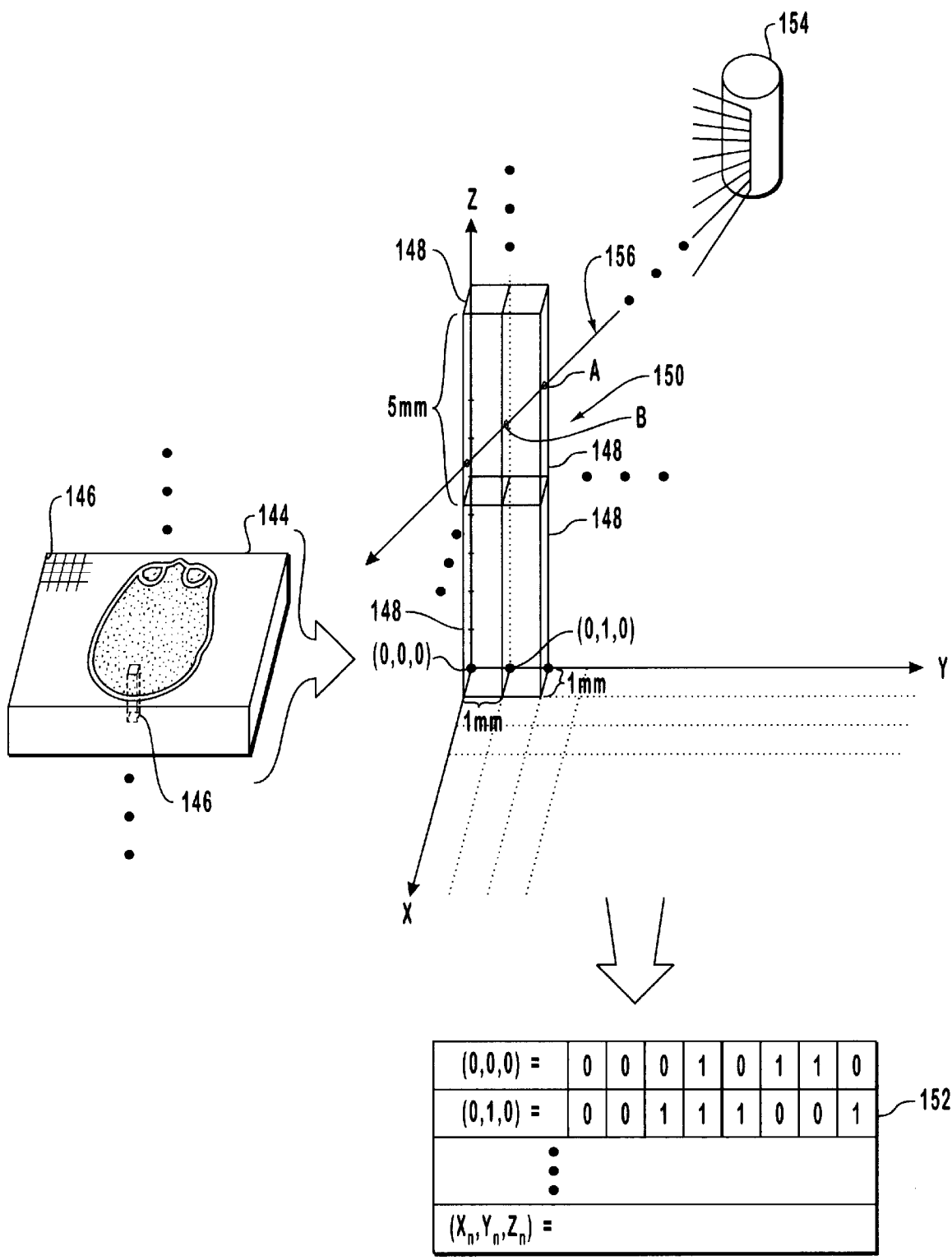
FIG. 5 is an exemplary diagram for converting pixels of medical imagery into a geometric model and for mapping the pixels into an array of anatomical materials in accordance with the present invention.

A diagram of the foregoing modeling of imagery is illustrated with reference to FIG. 5. In FIG. 5, a singular axial slice 144 representative of any of a variety of cross-sectional slices from a medical image is depicted as having a plurality of pixels 146. For clarity of the illustration, only a small portion of the pixels are shown with only one pixel being shown near the central portion of the axial slice 144.

The pixels 146 are converted into a plurality of univels 148. In this embodiment, each univel 148 is typically about 1 mm×1 mm×5 mm respectively along the X-, Y- and Z-axes.

Since each axial slice 144 is part of a larger medical image, as indicated by ellipses, each pixel 146 of each axial slice 144 is converted into univels 148 which, in turn, are stacked into a geometric model 150 of the treatment area planned for irradiation during the cancer therapy. In this embodiment, the geometric model 150 is represented by four univels 148 (two univels beneath two univels) but it should be appreciated that the univels extend outward in each of the X, Y and Z directions as indicated by ellipses. As used herein, "geometric model," "pixel of information," "anatomical material" and "treatment volume" may alternatively be referred to as a "model," "pixel," "material" or "irradiation volume," respectively. These alternative forms are useful for brevity or because of their common association amongst those skilled in the art.

Once the univels are mathematically stacked into the geometric model of the treatment volume, the anatomical materials represented by the univels are mapped to an array 152. Many mapping schemes are available and in this embodiment, a useful scheme uses a corner coordinate of each univel to identify the anatomical material thereof. For example, corner coordinate (0,0,0), corresponding to the X, Y and Z axes of the illustrated Cartesian coordinate system, is mapped to a binary representation of the number 22. The corner coordinate (0,1,0) is mapped to a binary representation of the number 57. These numbers preferably correspond to a look up table stored as part of the computing system configuration as part of either the local or remote storage devices. Thus, it should be appreciated that at least 256 different representations of anatomical material can be represented in this embodiment. In this embodiment, 22=scalp and 57=skull and other number representations are available for various other anatomical materials. This mapping continues until all anatomical materials of the univels have been mapped illustrated by ellipses continuing to corner coordinates $(X_n, Y_n, Z_n)$. This mapping, however, should not be construed as limiting. For example, the mapping could occur to a centered coordinate of each univel or any other useful scheme. Moreover, the described Cartesian coordinate system could be replaced with other coordinate systems such as a vector magnitude/angle coordinate systems and still maintain its usefulness. The foregoing mapping schemes and coordinate systems are exemplary and should not be construed as limiting.

By geometrically modeling the treatment area in this manner, it should be appreciated that the following advantages are realized over the prior art: (i) more than three anatomical materials are represented by the geometric model which ultimately improves radiation dosage accuracy; (ii) no loss of accuracy in modeling is introduced because of the one-to-one correspondence with the medical image pixels; (iii) time is preserved during the modeling because no intermediate steps are required to correlate pluralities of pixels to the elements used to geometrically model the treatment volume; (iv) any pertinent medical imagery can be accurately modeled without restriction; and (iv) all known information is utilized when computing dosimetry plans for clinical or research use. Yet, the foregoing is merely representative of some of the advantages.

Once the geometric model 150 is generated and the anatomical material of the univels are mapped, simulated transports or movements of "particles" are tracked or followed through the geometric model to ascertain, among other things, how a photon or neutron would travel through the model to ultimately find a representative distribution of radiation doses useful during cancer therapy. As described herein, neutrons emanating from a neutron source 154 during BNCT will be the "particles" that are used to exemplary describe the present invention.

As such, a beam of neutrons penetrates the treatment volume, represented by the geometric model 150 comprised of univels 148, and each particle of the beam can be identified by movement along a unique particle track 156. In general, the particle enters a starting element of the univels at point A and traverses through the univel into a next univel at position B. From position B, the particle traverses from the previous univel into the next element of the univels and continues until either the particle exits from the geometric model or is captured by the anatomical material of the univel.

It should be appreciated, however, that although the particle is described as traversing along the particle track, the particle transport through the model is preferably just a simulation of how a particle would travel through the model during therapy. The simulation is preferably effectuated by means of computer executable instructions input to the computing system configuration described in the context of the exemplary operating environment. Thus, the particle movement along the particle track, as described herein, may be either a simulated or an actual movement.

Sources for generating neutrons are well known and are exemplified by the Brookhaven Medical Research Reactor at the Brookhaven National Laboratory. As such, the neutrons sources 154 and their corresponding methodologies are not described herein in detail.

Figure 6A:
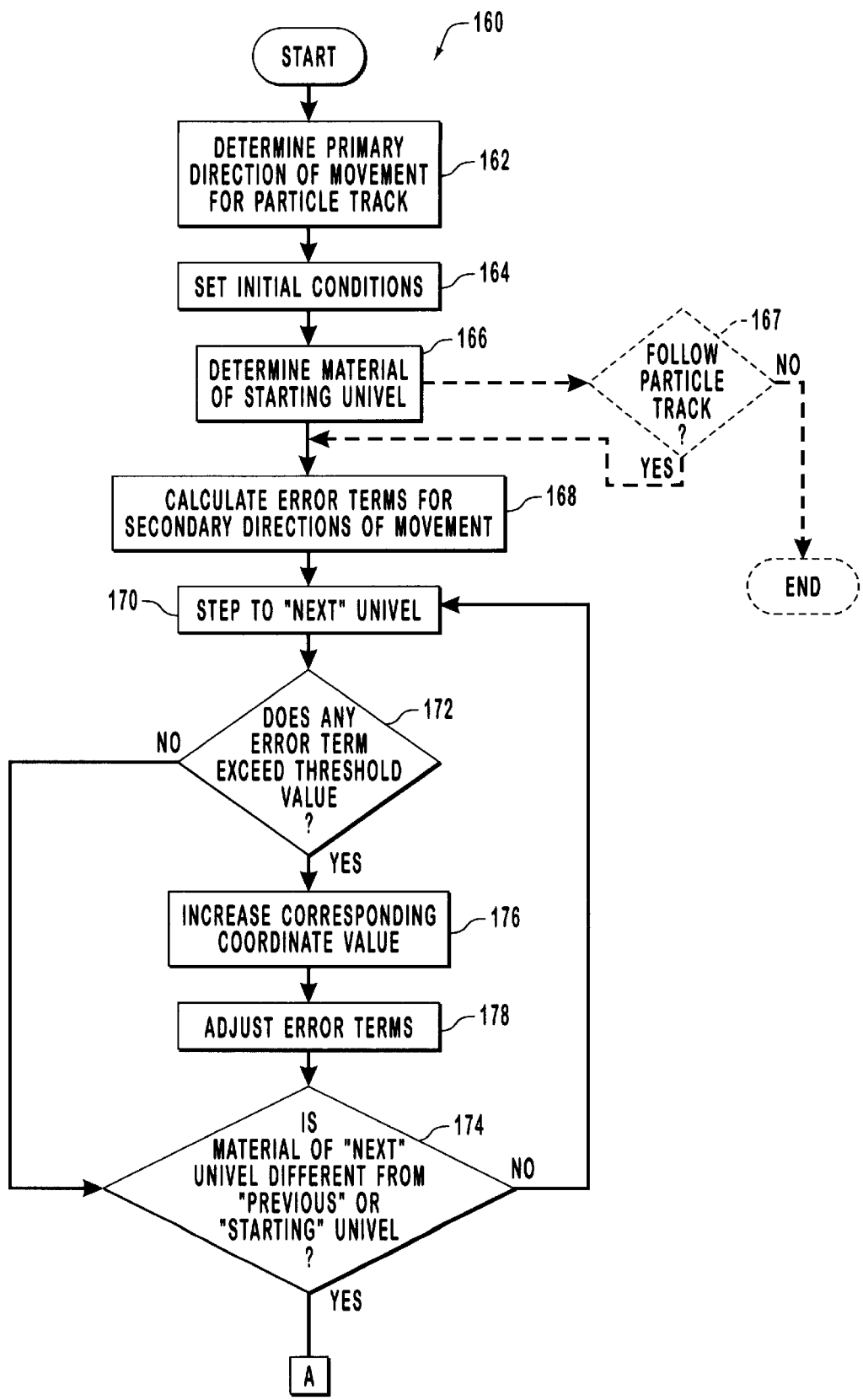
FIG. 6A is a first portion of a flow diagram for calculating particle transport simulations through a geometric model of a planned irradiation volume in accordance with the present invention.
Figure 6B:
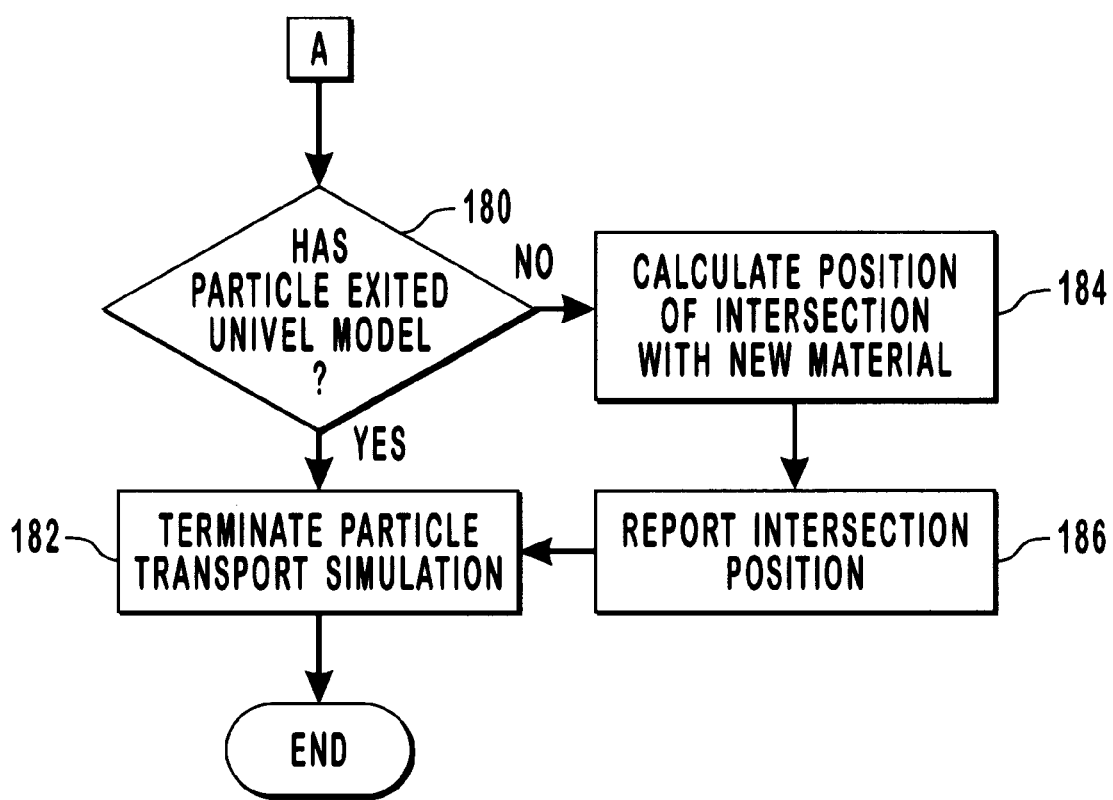
FIG. 6B is a second portion of a flow diagram for calculating particle transport simulations through a geometric model of a planned irradiation volume in accordance with the present invention.

With reference to FIGS. 6A and 6B, a method for tracking a singular particle through the geometric model 150 until the particle is exited or intersected with a new material, i.e., absorbed or scattered, is depicted generally as 160.

Figures 1, 2:
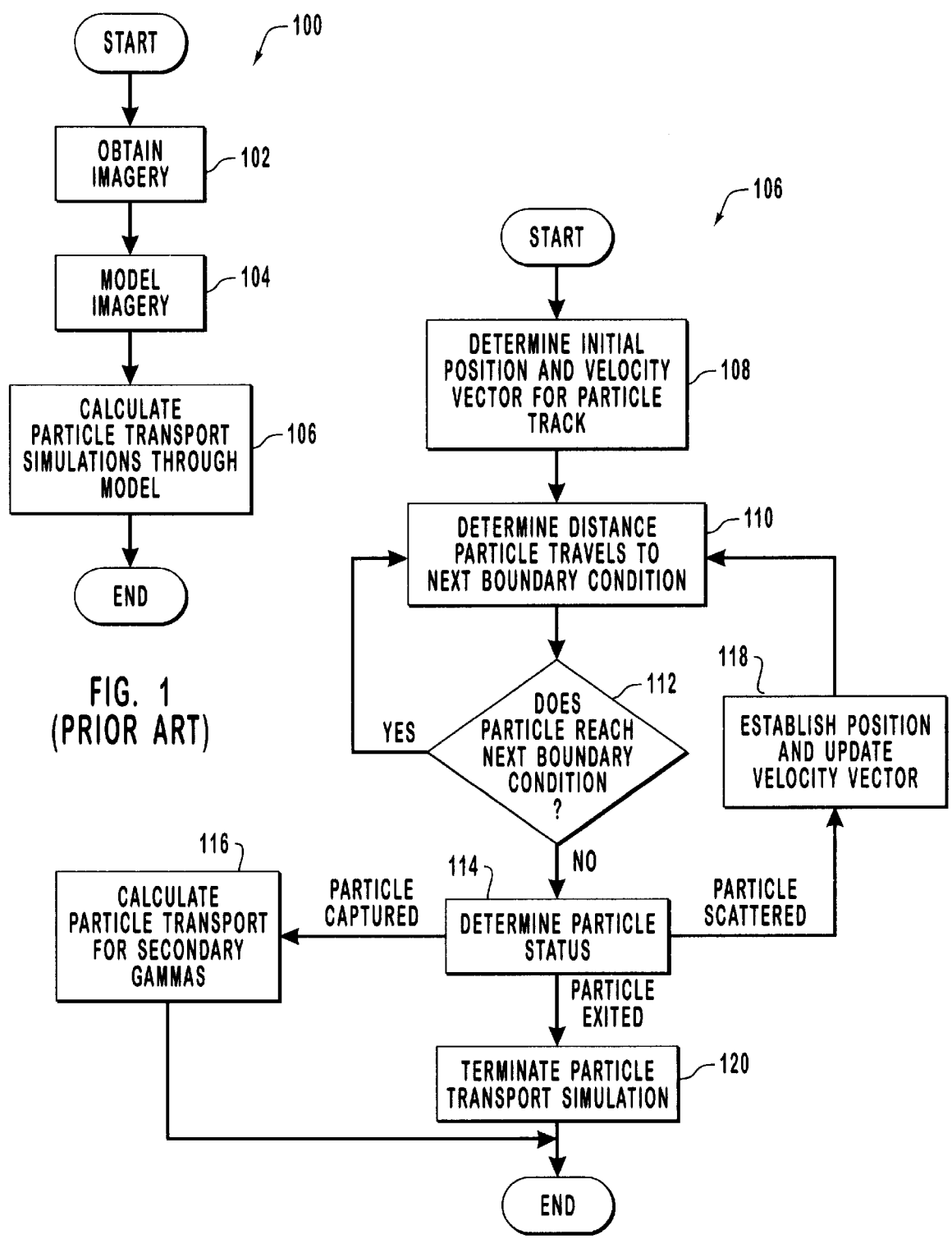
FIG. 1 is a flow diagram of a known method of computationally achieving a macrodosimetry plan.
FIG. 2 is a flow diagram of an exemplary hierarchical operation of calculating particle transport simulations through geometric models as invoked by the prior art routine of FIG. 1.

As described in the background section (FIG. 2), the calculations for simulated particles transported through a model begin with an initial position and velocity vector. This step is assumed as given for the following discussion. As another given, it is assumed that the initial position of the particle movement along the particle track is within the starting element of the univels (hereinafter starting univel).

At step 162, no matter which univel is the starting univel, a primary direction of movement for the particle along the particle track is determined from which a set of initial conditions can be established 164. Setting initial conditions once will later enable the quick and efficacious tracking of a movement of the particle through the geometric model. To further illustrate this, in FIG. 7, an exemplary particle track is depicted in three dimensions of a Cartesian coordinate system as particle track 200. The particle track 200 is depicted in two dimensions, in the X-Y plane, as particle track 202. From this illustration, it is seen that the track advances in the greatest intervals in the positive Y direction of travel. Thus, the primary direction of movement is in the positive Y direction and the initial conditions will be established in accordance with this positive Y direction. Whatever other directions of movement remain, here the X and Z directions, are termed the secondary and tertiary directions of movement, or vice versa depending upon how classified.

From the figure, the initial Y coordinate is $y_0=1.8$, which is somewhere in the starting univel, and the initial X and Z coordinates, $x_0$ and $z_0$, are some values along the particle track. The next step in setting the initial condition is to create a center value coordinate in the primary direction of movement. Centering is done to ensure that the particle track is sampled at representative points, of which, the center is more representative than either end. This is done by choosing the center value between integer values. Thus, since $y_0=1.8$, y is between integers 1 and 2, such that: $1 \leq y_0 < 2$, the center value is 1.5 This center value is a portion of the adjusted coordinate from which the particle movement along the particle track will begin and is designated as $y_1=1.5$. The values for the X and Z directions are needed to represent the entire adjusted coordinate.

Since the particle track 200 is a straight line, the line is merely extended to the adjusted coordinate as indicated by dashed line 204 in the both three and two dimensions. With $y_1=1.5$ as given, $x_1$ and $z_1$ are computed. From FIG. 7, it can be read that $x_1=3.5$ and $z_1=5.6$. Such coordinates are logged in table 210 in FIG. 7.

Figure 7:
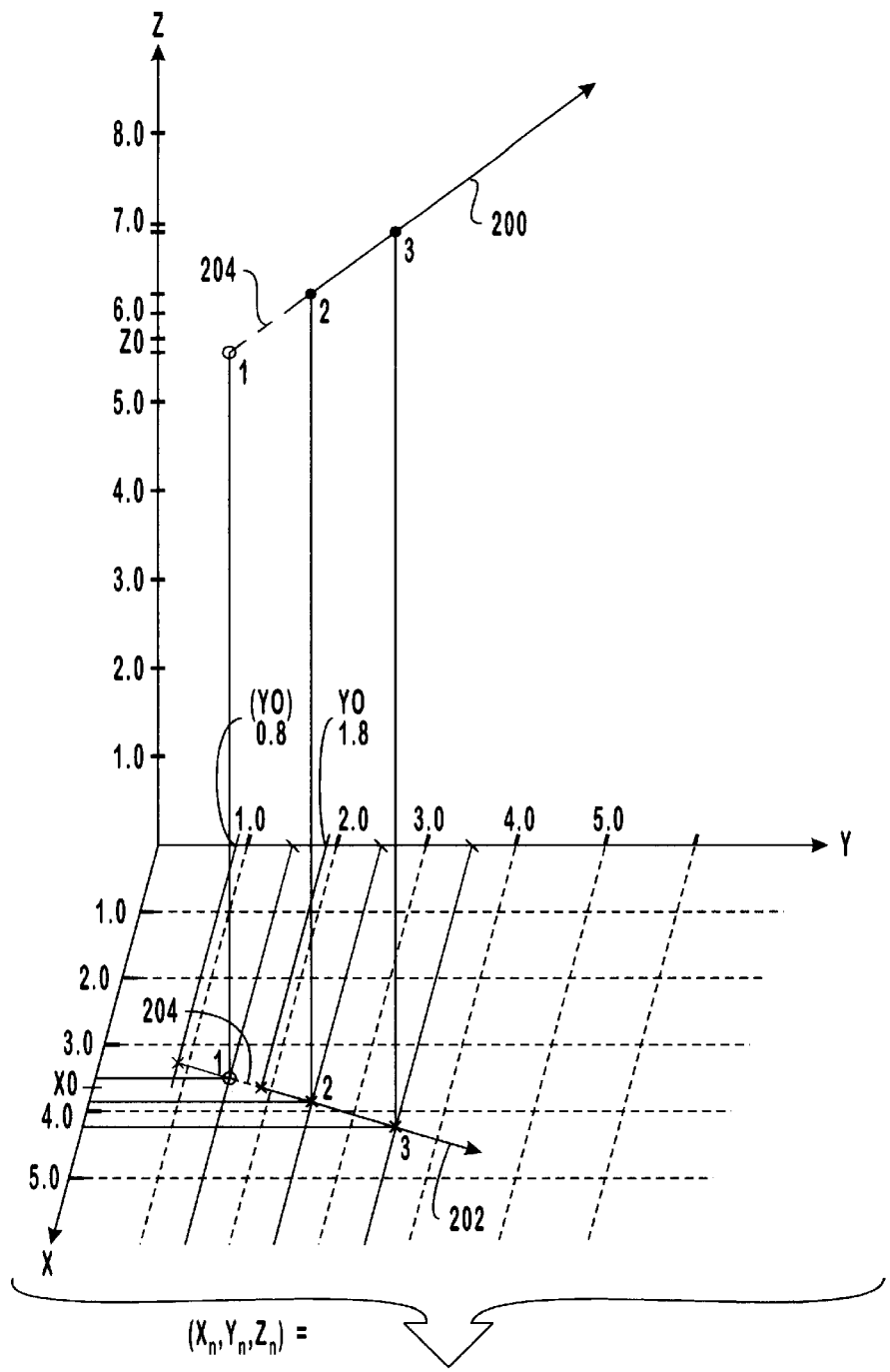
FIG. 7 is an exemplary diagram for depicting the primary direction of movement of a particle track, for setting the initial conditions and for stepping through univels during particle transport simulations as invoked by the routine of FIG. 6.

Thereafter, in FIG. 6 at step 166, the anatomical material of the starting univel is determined by reading the anatomical material from the array. Since, the array was mapped using integers, the anatomical material of the starting univel is easily determined by rounding each of the coordinates ($x_1$, $y_1$, $z_1$) down to the nearest integer. As such, for (3.5, 1.5, 5.6) the starting material of that univel is found in the array at (3,1,5) as illustrated in table 210 (FIG. 7).

Perhaps not readily apparent, the advantage of this is found as a result of the way computing system configurations perform calculations. For example, although a computer could determine the anatomical material of the univel from the coordinates (3.5, 1.5, 5.6) it is easier for a computer if floating point mathematics is not involved when computing and storing. Thus, by determining the anatomical material of the univels with integers, valuable computational time is preserved for other calculations and clinical uses.

Alternatively, it should be appreciated that the same center coordinates could be selected if, for example, the initial Y coordinate is $y_0=0.8$. Then, since $y_0 0.8$, the two nearest values centered in a univel along the Y axis are $y=0.5$ and $y=1.5$. If the primary direction of movement for the particle track was directed negatively along Y, then $y_1=0.5$ would be used. Since the particle track is positively directed, however, $y_1=1.5$ is the first centered value in the primary direction of movement. Again, with an extension of the particle track, the initial $x_1$ and $z_1$ coordinates can be read.

It should also be appreciated that an alternative method of determining the anatomical material of the starting univel could also be accomplished by using an integer floor or ceiling value of the univel containing the initial point. With this alternative, it is even within the scope of the present invention that steps 162 and 164 could be interposed such that the anatomical material of the starting univel is determined before setting the initial conditions.

As the particle is tracked, it is evident that coordinates corresponding to the secondary and tertiary directions of movement will need to be updated as the primary (Y) coordinate is tracked in integer based increments. Since the secondary and tertiary directions of movement are treated in the same manner, they will be described hereinafter as secondary directions of movement. Thus, at step 168, error terms are calculated for the secondary directions of movement to keep track of when either should be independently incremented. Preferably this adjustment occurs if either exceeds a predetermined threshold.

Thereafter, at step 170, the movement of the particle along the particle track is traversed in integer based increments along the primary direction of movement into the "next" univel. In this context, this traversal is also referred to as a "step" since it occurs in integer based increments.

Thus, with reference to the table 210 (FIG. 7), the traversal of the particle along the particle track steps in the Y direction according to $y_1=1.5$, $y_2=2.5$, $y_3=3.5$ until the ending element of the univels is reached where $y=y_n$. Although the integer steps are described herein as positive 1, it should be appreciated that the integers can be negative and can be in other logical values. It should also be appreciated that the integer values that are stored need not correspond to centered values along the primary direction of movement. It is just that the centered values provide the most representative sampling along the particle track.

Having stepped to a "next" univel at step 170, it is determined, at step 172, whether any of the error terms exceed the threshold value. If the error terms do not exceed the threshold values, a determination about the anatomical material of the next univel is made at step 174 to see if it is different from the previous or starting univel. Again, this is simply done by using the stored integer position values to examine the anatomical material mapped in array 152 for that univel against the previous univel. The actual points examined are expressed as floats but are only kept track of as integers. Thus, as in table 210 (FIG. 7), for the next univel having coordinates of (3.83, 2.5, 6.26) the anatomical material for that univel is stored in the array at (3,2,6) and a comparison between anatomical materials is made against (3,1,5). Similarly, for the univel having coordinates (4.13, 3.5, 6,93) the anatomical material for that univel is stored in the array at (4,3,6).

Because of the eventual possibility that stepping in the primary direction of movement without stepping along the particle track in the secondary direction of movement will cause an error in determining the anatomical material of the univel under examination, at step 172, if the error term exceeds the threshold value, an increase in the corresponding coordinate value is performed (step 176) to ensure the proper univel is being examined. Thereafter, at step 178, an adjustment of the error terms is performed to account for the increase in the corresponding coordinate value. Although not shown, the error term could also be adjusted to indicate that stepping only occurred in the primary direction of movement. Thence, once adjusted, the determination of the anatomical material of the next univel is made at step 174.

It should be appreciated that the anatomical material of the "next" univel is made in comparison to the starting univel, or, as the movement of the particle is tracked along the particle track, is made in comparison to the previous univel. If, at step 174, the anatomical material is not at least substantially different, the movement of the particle along the particle track is reiteratively traversed to the next univel (step 170) until eventually the particle exits the geometry or intersects with a new material.

Thus, at step 174, if the anatomical material of the next univel is different from the previous or starting univel, a determination is made, at step 180, to see if the particle has exited the geometric model. As in the prior art, if the particle has exited the geometric model, the particle transport simulation is terminated at step 182.

If the particle has not exited the geometric model at step 180 and the anatomical material of the next univel is different from the previous univel, the position of intersection with the new material is determined at step 184. When determined, this position of intersection is reported at step 186 for use in another part of the computer executable instructions. An example of this is when the particle is determined to be captured and the particle transport is determined for secondary gammas.

It should be appreciated from the foregoing that computational time is greatly preserved by stepping through the geometric model in integer based increments because each of the stepping computations and each determination about the anatomical material of each univel is performed by the computer without requiring the use of floating point mathematics. Thus, a medical image having pixels of information in 512×512 resolution×512 axial slices, millions of computations are performed over the course of numerous particles emanated from a neutron source. As described subsequently, this reduction in tracking time has been shown to be at least one order of magnitude faster than any computations heretofore known in the field.

Figure 8:
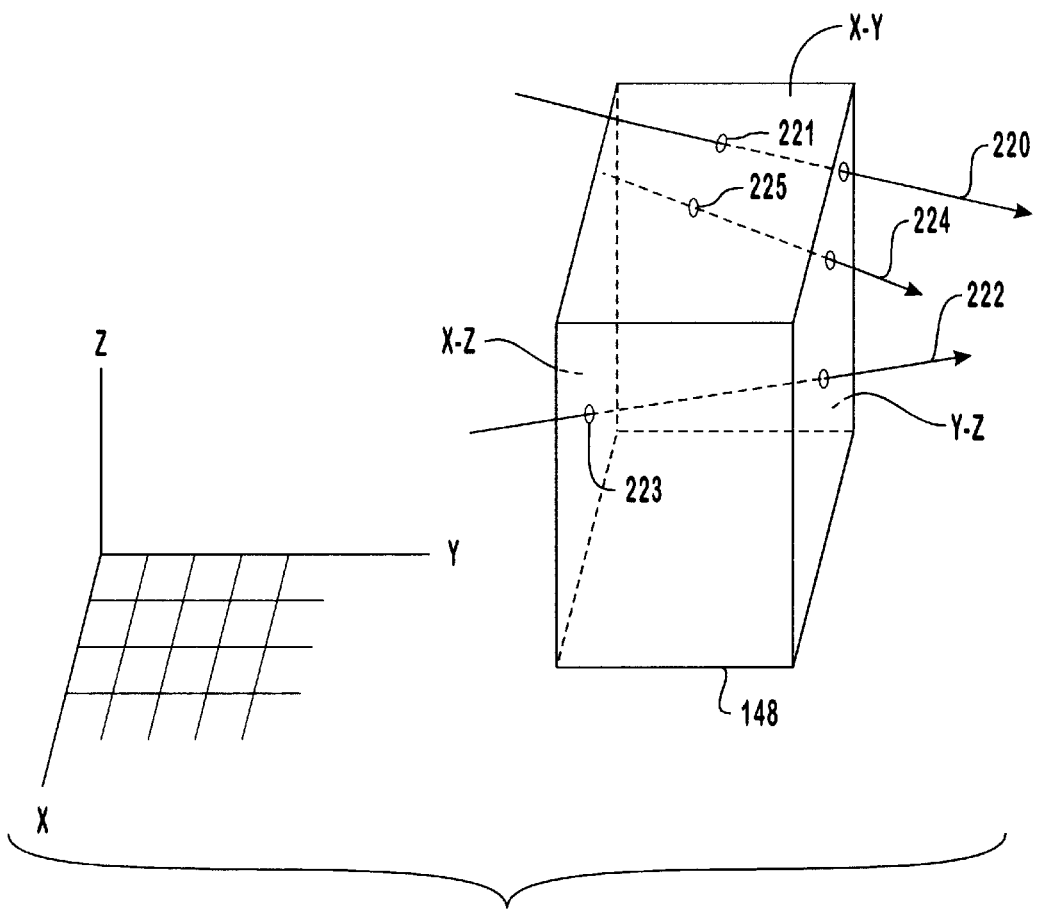
FIG. 8 is a diagram useful in describing the calculation of an intersection position along a particle track between various anatomical materials as invoked by the routine of FIG. 6.

The step 184 for determining where the position of intersection with the new material happens, is further described with reference to FIGS. 8 and 9. In FIG. 8, it is known that in some univel 148, the particle traveling along the particle track entered an anatomical material different from the previous univel. To determine the precise intersection, it is first known that the particle entered the univel 148 along the particle track through one of three planes. The particle may have entered the univel: through the X-Y plane as along particle track 220; through the X-Z plane along particle track 222; or through the Y-Z plane along particle track 224. The X, Y and Z planes being taken in reference to the Cartesian coordinate system depicted. Again, other coordinate systems can be used.

Figure 9:
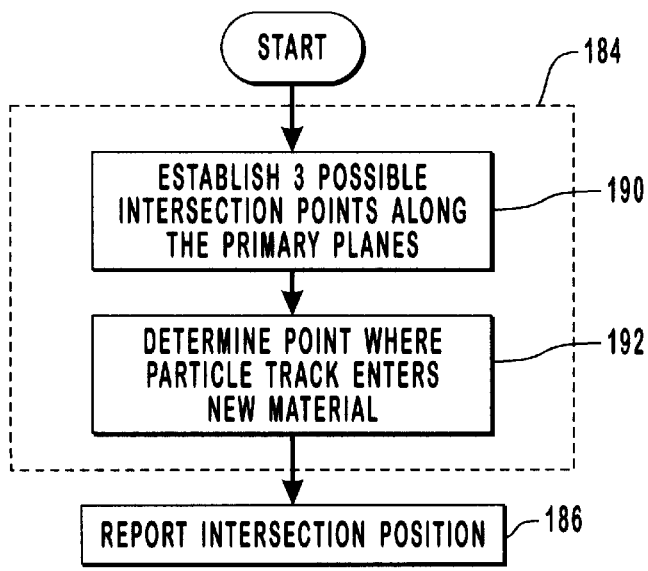
FIG. 9 is a flow diagram for calculating an intersection position between various anatomical materials as invoked by the routine of FIG. 6.

In a preferred embodiment, with reference to FIG. 9, three possible intersection points are established along the three primary planes described above, step 190. For example, the first position is 221 along particle track 220. The second position is 223 along particle track 222. The third position is 225 along particle track 224. Since each of these three positions are along a planar surface of a univel, a small epsilon may be added to move each of the three positions inside the univel by a small amount so that ambiguity of being on the planar surface can be avoided for computational purposes.

In a preferred embodiment, the three positions correspond to a floor or ceiling operator. The floor or ceiling is in reference to whether the particle track is moving in positive or negative increments. If positive, a floor is set. If negative, a ceiling is set. An example of this is depicted by particle track 222 in which positive increment advancement occurs in the Y and Z directions and negative increment advancement occurs in the X direction. Then, at step 192, determine the position where the particle track first enters the new material. This is done by examining whichever particle through one of the three positions first hits or intersects the anatomical material that is different from the previous univel, this is the position of intersection. Again, this intersection position is reported at step 186. Floor and ceiling operators are well known in the art and are not described herein in detail.

Figure 10:
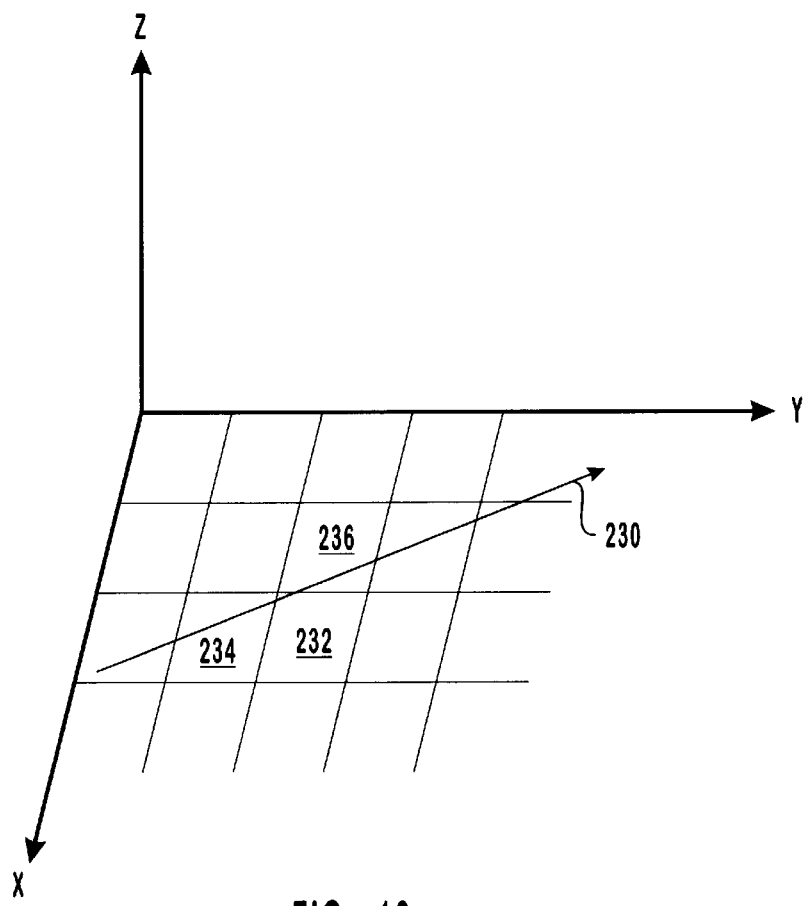
FIG. 10 is a diagram of a skipped univel in accordance with a preferred embodiment of the present invention.

With this method of integer based tracking of a movement of a particle along a particle track through a geometric model, it should be appreciated that some univels may be skipped over when tracking the particle. An example of this is shown with reference to FIG. 10, wherein a particle track 230, shown only in the X-Y plane, traverses through a small corner of univel 232. As such, if univel 232 is of the same anatomical material as univel 234, there is no need to perform a detailed examination regarding this univel and progression of the particle track can continue to univel 236. Thus, it is only when a univel has a different anatomical material from the previous univel that any further detailed calculations are required to be made. If the anatomical material of univel 232 is different, but the particle track reenters the original material in univel 236, then an insufficient volume in 234 was intersected to count as a boundary crossing. In the case where the anatomical material of 236 is different than 234, univel 232 will also be examined when determining the precise crossing into the new material since three planes of entry into the new material are considered. Again, when calculations for particle tracks are performed through millions of univels, tremendous computational time is saved.

In contrast to the prior art, it should be appreciated that computational accuracy is improved with more representations of the treatment volume than with fewer. For example, some methods in the prior art used 500 pixels as a single element representation for tracking a particle movement. Yet, in a 256×256 resolution, this only equates to about 130 elements in the model. If a particular particle track only passed through a small portion of these 130 elements, an accurate understanding required for computational dosimetry would be severely lacking. Yet here, a 256×256 resolution equates to 65,536 univels per axial slice. But because the tracking is performed in integer based increments, the tracking is not only faster but yields more accurate data in the dosimetry planning.

In an alternate embodiment, after step 166 (FIG. 6A), a decision 167 is made whether to follow along the particle track or not. When performing Monte Carlo simulation using an alternative scheme known as "boundary elimination," it is only necessary to know the material of the starting univel and not required to follow along the particle track to determine the next material intersection. Thus, for this alternate method, and for some editing purposes, return is made to the calling program immediately after determining the material of the starting univel. As such, this alternative step is indicated by dashed lines.

Figure 11:
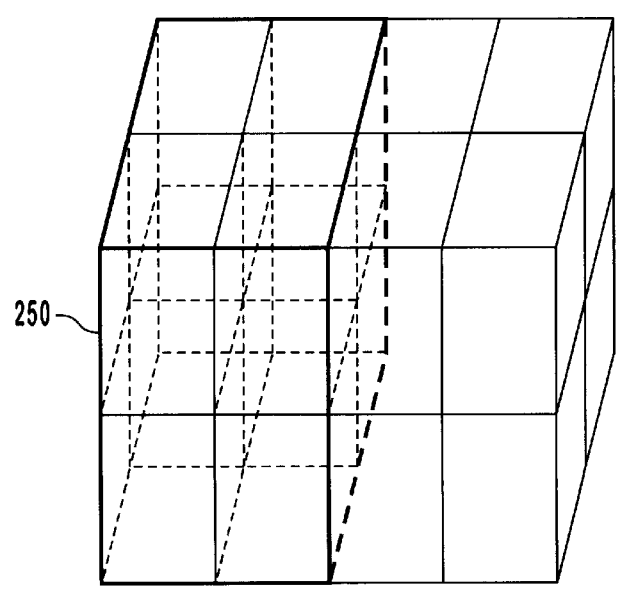
FIG. 11 is a diagram of a univel useful in calculating particle transport simulations through a geometric model when provided medical imagery has very fine resolution capabilities in accordance with an alternative embodiment of the present invention.

With reference to FIG. 11, it should be appreciated that as medical imagery becomes even more sophisticated, it is expected that even greater resolutions will be provided, such as in a 1000 pixel×1000 pixel resolution with 1000 axial slices. Thus, to improve computational times for tracking a particle movement through the geometric model, groupings of elements may be advantageously arranged. One such grouping uses a super univel 250 comprised of an arrangement of smaller univels in a 2×2×2 configuration. Still other combinations of univels can be effectuated.

EXAMPLE 1

The following represents data obtained from tracking a movement of 100,000 particles along random particle tracks (Monte Carlo simulated) through a geometric model constructed from a 256×256×33 medical image consisting of a buffer material, scalp, skull, brain and tumor anatomical materials.

The particle tracks began at a random initial position in the geometric model and traversed in a random direction. Each movement was tracked along the particle track until either the particle intersected an anatomical material different from the anatomical material of the previous univel or was exited from the geometric model. Of the 100,000 particle tracks, 55,137 positions of intersections and 44,863 exits from the geometric model were reported.

TABLE 1

| | |
|---|---|
| 3,600,422 | univels having particle tracks |
| 33,670.034 | positions of intersection/sec |
| 1,212,263.3 | univels/sec |
| 36.004 | univels tracked through/position of intersection reported |
| 2.970 | elapsed time (sec) |
| 196,270.562 | distance traveled all particle tracks (cm) |
| 66,084.364 | distance traveled/sec |

It should be appreciated that since the simulated particle transport was performed in less than about 0.2 hours, the foregoing represents an advance over the present state of the art by as much as 51 times. Heretofore, such simulated particle transport would routinely require as much as 10 hours of computational time or more.

EXAMPLE 2

The following represents the actual algorithm information used to simulate such advanced particle transport along a particle track as planned for presentation at the 1998 Radiation Protection and Shielding Division Topical Conference in Nashville, Tenn. in April.

Data Initialization

The uniformly spaced medical image data is read into an array. The x-pixel-size, y-pixel-size, and z-pixel size along with the minimum value of each coordinate is stored so conversions between world coordinates (WC) and normalized array coordinates (NAC) can be easily made. Here, the NAC simply corresponds to a location in the array of univels. For example, any location in the array can be found by an ordered triple of nonnegative integers, i.e., lookup (x,y,z)=array (z(width×length)+y(width)+x). A univel in WC is A mm×B mm×C mm. Whereas the univel in NAC is 1×1×1, for example.

Parameters

A call to the movement of the particle along a particle track is of the form:
  Track_Ray (position_vector, direction_unit_vector, ptr_to_miss_flag, ptr_to_current_region, ptr_to_next_region, ptr_to_distance_to_next_region);

Input to Algorithm
  position_vector: Initial position of particle track in WC
  direction_unit_vector: Normalized direction of particle track in WC Output of Algorithm
  miss_flag: Either hit a new region or exit the geometric model
  current_region: The region (univel) the particle track starts in
  next_region: The first region intersected
  distance_to_next_region: The distance to the next_region (univel) in WC Algorithm Initialization Calculations The initial position and direction must be converted from WC to NAC. The initial anatomical material is stored in current_region. If the particle track does not start inside the univel geometric model, an intersection point with the univel geometric model must be calculated and an artificial starting point is set at this boundary intersection with the outer univel.

Stepping Algorithm

Though the internal routines of the algorithms vary, each is based on using integer arithmetic to find univels that the ideal particle track passes through. Each investigated univel has a corresponding call to a function that looks up the anatomical material type of the univel at the given position. The stepping algorithm terminates when a univel of a new anatomical material type is found or the particle along the particle track exits the geometric model.

Algorithm Completion Calculations

The position of intersection is computed accurately or miss_flag is set to indicate the particle exited the geometric model without an intersection. The distance to this point is calculated in WC and returned in distance_to_next_region. The new material encountered is stored in next_region.

EXAMPLE 3

The following data is as planned for presentation at the 1998 conference in Nashville, Tenn. and is exemplary of a particle track having Y as a primary direction of movement, X is the secondary direction of movement increasing in 0.125 units of a Cartesian coordinate system and Z is the tertiary direction of movement increasing in 0.75 units. The initial starting position of the particle track after centering is $x_0=5.00$, $y_0=1.5$ and $z_0=10.125$. Truncating (trunc) is the rounding down function. Stepping along the primary direction of movement yields the following data with an error term being an integer in the range of −32,768 to 32,767:

TABLE 2

| x | y | z | trunc(x) | trunc(y) | trunc(z) |
|---|---|---|---|---|---|
| 5.000 | 1.5 | 10.125 | 5 | 1 | 10 |
| 5.125 | 2.5 | 10.875 | 5 | 2 | 10 |
| 5.250 | 3.5 | 11.625 | 5 | 3 | 11 |
| 5.375 | 4.5 | 12.375 | 5 | 4 | 12 |
| 5.500 | 5.5 | 13.125 | 5 | 5 | 13 |
| 5.625 | 6.5 | 13.875 | 5 | 6 | 13 |
| 5.750 | 7.5 | 14.625 | 5 | 7 | 14 |
| 5.875 | 8.5 | 15.375 | 5 | 8 | 15 |
| 6.000 | 9.5 | 16.125 | 6 | 9 | 16 |

The bulk of the corresponding stepping algorithm for this example is as follows:

```
ADDX=0.125*32768=4096
ADDZ=0.750*32768=24576
ADDX_DECERR=ADDX−32768
ADDZ_DECERR=ADDZ−32768
ERRX=(x0−trunc(x0))*32768+ADDX_DECERR=−28672
ERRZ=(z0−trunc(z0))*32768+ADDZ_DECERR=−4096
XI=trunc(x)
YI=trunc(y)
ZI=trunc(z)
BEGIN_LOOP
LOOKUP(XI,YI,ZI)
YI=YI+1
If (ERRX>=0)
XI=XI+1
ERRX=ERRX+ADDX_DECERR
Else
ERRX=ERRX+ADDX
If (ERRZ>=0)
ZI=ZI+1
ERRZ=ERRZ+ADDZ_DECERR
Else
ERRZ=ERRZ+ADDZ
END_LOOP
```

The next table shows the values computed by the algorithm. Notice that the error term, i.e., ERRX or ERRZ, is a pre-computation used to determine how XI and ZI will change in the next iteration, increasing by 1 if the error is greater than or equal to 0 and remaining the same otherwise. The steps are similar when the directions are allowed to be decreasing.

TABLE 3

| XI | YI | ZI | ERRX | ERRZ |
|----|----|----|------|------|
| 5 | 1 | 10 | −28672 | −4096 |
| 5 | 2 | 10 | −24576 | 20480 |
| 5 | 3 | 11 | −20480 | 12288 |
| 5 | 4 | 12 | −16384 | 4096 |
| 5 | 5 | 13 | −12288 | −4096 |
| 5 | 6 | 13 | −8192 | 20480 |
| 5 | 7 | 14 | −4096 | 12288 |
| 5 | 8 | 15 | 0 | 4096 |
| 6 | 9 | 16 | −28672 | −4096 |

This example was for each x, y and z increasing and y varying the most. The method would be similar for either x or z varying the most. Negative directions only cause minor complications wherein absolute values of the directions are used to compute the ADDx's. ERRx's are computed based on the distance to the ceiling side rather than the floor side of the initial univel from the initial point.

In the general case, there is some roundoff error since the initial positions and increments may not be expressed exactly as fractions of 32768. Using 32 bit arithmetic instead, an individual error is less than $2^{-31}(\approx 4.66*10^{-10})$ and the error accumulates by at most that much on each iteration. In a 256×256×40 array of univels, the cumulative error could at worst be $256*2^{-31}=2^{-23}(\approx 1.19*10^{-7})$ which is insignificant in most cases for two reasons. The algorithm yields only an approximate x, y, and z as an array position which is then refined to give a precise intersection that is not subject to this cumulative error. Also, the approximated particle movement follows very closely the same univels as the ideal particle track. Being off by at most $2^{-23}$ of a side length suggests that the approximate particle track reports a position of intersection not intersected by the ideal particle track less than 1 in 1,000,000 times. If the algorithm reports a position of intersection that is not verifiable, the particle movement along the particle track is simply allowed to continue. Any position of intersection distance returned is precise and verified.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A method for tracking a movement of a particle through a geometric model so as to facilitate development of a dosimetry plan, the steps comprising:
    arranging a plurality of substantially uniform volume elements into said geometric model;
    describing said movement of said particle through said geometric model with a particle track, said particle track having a primary direction of movement; and
    traversing said particle along said particle track in integer based increments along said primary direction of movement.

2. A method according to claim 1, further comprising the step of converting a plurality of pixels of information contained in a medical image into said uniform volume elements.

3. A method according to claim 1, further comprising the step of defining a material to be associated with each said uniform volume element.

4. A method according to claim 3, further comprising the step of mapping each said material to an array.

5. A method according to claim 1, wherein said particle traverses along said particle track from a previous element of said uniform volume elements to a next element of said uniform volume elements, further comprising the steps of:
    determining a material of both said previous and said next elements; and
    terminating said step of traversing said particle when said material of said next element is substantially different from said material of said previous element.

6. A method according to claim 5, further comprising the step of determining a position of intersection along said particle track where said material of said previous element changed into said material of said next element.

7. A method according to claim 6, further comprising the step of reporting said position of intersection.

8. A method according to claim 1, wherein said particle traverses along said particle track from a previous element of said uniform volume elements to a next element of said uniform volume elements, further comprising the steps of:
    determining a material of both said previous and said next elements; and
    when said material of said next element is substantially similar to said material of said previous element, reiteratively traversing to another next element of said uniform volume elements along said particle track.

9. A method according to claim 1, further comprising the step of setting an initial condition for said particle track.

10. A method according to claim 9, wherein said particle traverses along said particle track beginning in a starting element of said uniform volume elements and traverses to a next element of said uniform volume elements, further comprising the step of determining a center value of said starting element along said primary direction of movement, said center value representing at least a portion of an adjusted coordinate from which said particle will begin traversal along said particle track.

11. A method according to claim 10, wherein said particle track has at least one secondary direction of movement, further comprising the step of determining a beginning coordinate value for each said secondary direction of movement in response to said step of determining said center value of said starting element along said primary direction of movement.

12. A method according to claim 1, wherein said particle track has at least one secondary direction of movement, further comprising the step of calculating an error term for each said secondary direction of movement, said error terms being used to adjust a coordinate value whenever said error term exceeds a threshold value.

13. A method for simulating particle transport through a geometric model so as to facilitate development of a dosimetry plan, the steps comprising:
    arranging a plurality of substantially uniform volume elements into said geometric model, said geometric model corresponding to a coordinate system;
    defining a material to be associated with each said uniform volume element;
    describing a particle track with a primary direction of movement through said geometric model, said particle track beginning in a starting element of said uniform volume elements and traversing to a next element of said uniform volume elements; and following a particle along said particle track through said geometric model until said material of said next element is substantially different from said material of said starting element.

14. A method according to claim 13, wherein said step of describing said particle track comprises the steps of defining an initial position and a vector for said particle.

15. A method according to claim 13, wherein said step of defining said material to be associated with each said uniform volume element further comprises the step of mapping each said material to an array.

16. A method according to claim 13, wherein said step of following said particle along said particle track comprises the step of stepping along said particle track in integer based increments of said coordinate system along said primary direction of movement.

17. A method of developing a dosimetry plan for a treatment volume targeted for irradiation during radiation therapy, the steps comprising:
  obtaining a medical image of said treatment volume, said medical image containing a plurality of pixels of information;
  converting said pixels into a plurality of substantially uniform volume elements;
  arranging said uniform volume elements into a geometric model;
  defining a material to be associated with each said uniform volume element;
  describing a plurality of particle tracks through said geometric model, said particle tracks having a primary direction of movement beginning in a starting element of said uniform volume elements and traversing to a next element of said uniform volume elements;
  simulating a particle movement along each said particle track through said geometric model in integer based increments along said primary direction of movement until a position when said material of said next element is substantially different from said material of said starting element, said particle corresponding to a neutron emanating from a neutron source during said planned irradiation, said position corresponding to at least one of said neutron being captured, scattered and exited from said geometric model; and
  computing a distribution of radiation doses based upon said particle movement along each said particle track.

18. A method according to claim 17, further comprising the step of generating a plurality of axial slices of said treatment volume.

19. A method according to claim 17, wherein said step of converting said pixels into said uniform volume elements further comprises the step of proportionally converting a volume and shape of said pixels into a corresponding volume and shape of said uniform volume elements.

20. A computer readable medium having computer executable instructions for tracking a simulated or actual movement of a particle through a geometric model so as to facilitate development of a dosimetry plan, the computer executable instructions for performing the steps of:
  arranging a plurality of substantially uniform volume elements into said geometric model;
  mapping a material associated with each said uniform volume element to an array;
  projecting said movement of said particle through said geometric model with a particle track beginning in a starting element of said uniform volume elements and traversing to a next element of said uniform volume elements, said particle track having a primary direction of movement; and
  traversing said particle along said particle track in integer based increments along said primary direction of movement until said material of said next element is substantially different from said material of said starting element.

21. A computer readable medium according to claim 20, further comprising computer executable instructions for performing the step of storing said array in a storage device.

22. A computer readable medium according to claim 20, further comprising computer executable instructions for performing the step of establishing a center value for said particle track along said primary direction of movement, said center value representing at least a portion of an adjusted coordinate from which said particle traversal along the particle track begins.

23. A computer readable medium according to claim 20, further comprising computer executable instructions for performing the step of storing said array by integers determined from a selected coordinate system.

24. A computer readable medium according to claim 23, further comprising computer executable instructions for performing the step of computing error terms to be associated with at least one secondary direction of movement, said error terms being used to properly identify said materials stored in said array.

25. A computer readable medium according to claim 20, further comprising computer executable instructions for performing the steps of:
  reading a medical image having a plurality of pixels of information contained therein; and
  converting said pixels into said uniform volume elements.

26. A computer readable medium according to claim 25, further comprising computer executable instructions for performing the step of proportionally converting a volume and shape of said pixels into a corresponding volume and shape of said uniform volume elements.

27. A computer readable medium according to claim 25, wherein said medical image comprises a plurality of substantially cross-sectional slices of a treatment volume, further comprising computer executable instructions for performing the step of stacking said uniform volume elements into a three dimensional representation of said treatment volume.

28. A computer readable medium according to claim 20, firther comprising computer executable instructions for performing the step of displaying said geometric model.

29. A computer readable medium having computer executable instructions for developing a dosimetry plan for a treatment volume targeted for irradiation during cancer therapy, said computer executable instructions for performing the steps of:
  reading a medical image of said treatment volume, said medical image containing a plurality of pixels of information;
  converting said pixels into a plurality of substantially uniform volume elements;
  mathematically stacking said uniform volume elements into a geometric model substantially representing said treatment volume;
  mapping a material associated with each said uniform volume element to an array;
  describing a plurality of particle tracks through said geometric model, said particle tracks having a primary direction of movement beginning in a starting element of said uniform volume elements and traversing to a next element of said uniform volume elements;

simulating a particle movement along each said particle track through said geometric model in integer based increments along said primary direction of movement until a position when said material of said next element is substantially different from said material of said starting element, said particle corresponding to a neutron emanating from a neutron source during said planned irradiation, said position corresponding to at least one of said neutron being captured, scattered and exited from said geometric model; and computing a distribution of radiation doses based upon said particle movement along each said particle track.

30. A computer readable medium having computer executable modules for developing a dosimetry plan for a treatment volume targeted for irradiation during cancer therapy, comprising:

a reader module for converting a plurality of pixels of information contained in a medical image into a corresponding plurality of uniform volume elements;

a modeling module for stacking said uniform volume elements into a geometric representation of said treatment volume;

a storage module for storing information of a material for each said uniform volume elements;

a projection module for tracking a movement of a particle through said geometric representation along a primary direction of movement according to integer based steps along said primary direction of movement; and a random generation module for calculating a status of said particle as said movement of said particle is tracked through said geometric representation.

31. A method for developing a dosimetry plan for a treatment volume targeted for irradiation during cancer therapy, the steps comprising:

creating a geometric model of said treatment volume;

describing a movement having a primary direction thereof of a particle through said geometric model in integer based increments along said primary direction, said particle representing a neutron emanating from a neutron source during said irradiation; and computing a distribution of radiation doses based upon said movement of said particle.

32. A method according to claim 31, wherein said geometric model is comprised of a plurality of substantially uniform volume elements, further comprising the step of defining a material to be associated with each said uniform volume element.

33. A method according to claim 32, wherein said movement begins in a starting element of said uniform volume elements and traverses to a next element of said uniform volume elements, further comprising the step of describing said movement of said particle through said geometric model until said material of said next element is substantially different from said material of said starting element.

34. A method according to claim 33, further comprising the step of determining a position where along said movement said next element is substantially different from said material of said starting element.

35. A computer readable medium having computer executable instructions for performing the steps as recited in claim 34.

* * * * *